(12) United States Patent
Hibi (10) Patent No.: US 8,125,515 B2
(45) Date of Patent: Feb. 28, 2012

(54) ENDOSCOPE SYSTEM

(75) Inventor: Haruhiko Hibi, Tokyo (JP)

(73) Assignee: Hoya Corporation, Tokyo (JP)

( * ) Notice: Subject to any disclaimer, the term of this patent is extended or adjusted under 35 U.S.C. 154(b) by 1170 days.

(21) Appl. No.: 11/872,368

(22) Filed: Oct. 15, 2007

(65) Prior Publication Data

US 2008/0100699 A1     May 1, 2008

(30) Foreign Application Priority Data

Oct. 30, 2006   (JP) ................................. 2006-293639

(51) Int. Cl.
*H04N 7/18*     (2006.01)

(52) U.S. Cl. ............... 348/65; 348/72; 348/76; 600/101; 600/118; 600/132; 709/217

(58) Field of Classification Search ..................... 348/65, 348/72, 76, 66–69, 74; 600/101, 118, 132; 709/217–222
See application file for complete search history.

(56) References Cited

U.S. PATENT DOCUMENTS

| | | | | |
|---|---|---|---|---|
| 5,398,056 | A * | 3/1995 | Yabe et al. ....................... | 348/68 |
| 5,894,322 | A * | 4/1999 | Hamano et al. ................ | 348/68 |
| 6,322,496 | B1 | 11/2001 | Iida et al. | |
| 6,453,423 | B1 * | 9/2002 | Loison ........................... | 713/310 |
| 7,089,451 | B2 * | 8/2006 | Ote et al. ......................... | 714/31 |
| 7,171,568 | B2 * | 1/2007 | Dayan et al. .................. | 713/300 |
| 2005/0093973 | A1 | 5/2005 | Hibi et al. | |
| 2005/0097191 | A1 * | 5/2005 | Yamaki et al. ................ | 709/219 |
| 2007/0076091 | A1 | 4/2007 | Hibi | |

FOREIGN PATENT DOCUMENTS

| | | |
|---|---|---|
| JP | 11 318823 | 11/1999 |
| JP | 2001 449 | 1/2001 |
| JP | 2001 178685 | 7/2001 |

OTHER PUBLICATIONS

English language Abstract of JP 11-318823.
English language Abstract of JP 2001-449.
English language Abstract of JP 2001-178685.

* cited by examiner

*Primary Examiner* — Wing Chan
*Assistant Examiner* — Ruolei Zong
(74) *Attorney, Agent, or Firm* — Greenblum & Bernstein, P.L.C.

(57) ABSTRACT

An endoscope system, including a plurality of processor devices, each of which having a detachably attached endoscope, and a controller device, which is communicably connected with the plurality of processor devices, is provided. The controller device is capable of outputting at least one of an activating signal to activate at least one of the processor devices and an inactivating signal to inactivate at least one of the processor devices to the at least one of the processor devices. Each of the plurality of processor devices includes a first power supplying unit to supply the processor device with activating power, a power supply controlling unit, which is driven by preparatory power and is capable of at least one of switching on the first power supplying unit and switching off the first power supplying unit, and a second power supplying unit to supply the preparatory power to the power supply controlling unit.

10 Claims, 10 Drawing Sheets

ENDOSCOPE SYSTEM

BACKGROUND OF THE INVENTION

The present invention relates to an endoscope system having a plurality of processor units, and more specifically to power control of the plurality of processor units.

Conventionally, endoscope systems with endoscope units being installed in operation rooms for various operations such as inspections, surgeries, and medical treatments, have been used in many medical facilities. In such an endoscope system, the endoscope unit is connected with a controller provided in a remote administrating room so that various data, including image data obtained through the endoscope and information of the patient, can be exchanged between the controller and the endoscope unit through a communication line. An Example of such an endoscope system is disclosed in Japanese Patent Provisional Publication No. H11-318823. When such an endoscope system is provided with a plurality of endoscope units, each endoscope unit can be installed in an operation room respectively and connected to the controller to exchange the various data within the endoscope system through a network such as a LAN. An example of such an endoscope system is disclosed in Japanese Patent Provisional Publication No. 2001-449.

For the endoscope systems disclosed in the above-referenced publications, an operator is required to move to each operation room to switch power on in order to activate each endoscope unit. In addition, the endoscope units are required to be switched off after the operations, which can be troublesome specifically when the endoscope units are installed in remote operation rooms.

SUMMARY OF THE INVENTION

In view of the foregoing drawbacks, the present invention is advantageous in that an endoscope system with a power control unit capable of remotely controlling power supply to the plurality of processor units is provided.

According to an aspect of the present invention, there is provided an endoscope system, including a plurality of processor devices, each of which having a detachably attached endoscope, and a controller device, which is communicably connected with the plurality of processor devices. The controller device is capable of outputting at least one of an activating signal to activate at least one of the processor devices and an inactivating signal to inactivate at least one of the processor devices to the at least one of the processor devices. Each of the plurality of processor devices is provided with a first power supplying unit to supply the processor device with activating power, a power supply controlling unit, which is driven by preparatory power and is capable of at least one of switching on the first power supplying unit according to the activating signal and switching off the first power supplying unit according to the inactivating signal, and a second power supplying unit to supply the preparatory power to the power supply controlling unit.

Optionally, the at least one of the activating signal and the inactivating signal from the controller device may be output to a selectively specified processor device among the plurality of processor devices.

Optionally, the controller device may be capable of detecting power status of the at least one of the processor devices by transmitting detecting signals for detecting power status of the first power supplying unit of the at least one of the processor devices to the power supply controlling unit of the at least one of the processor devices, and receiving power status signals, indicating the power status of the first power supplying unit, transmitted from the power supply controlling unit.

Optionally, the controller device may detect power-on state of the at least one of the processor devices by receiving power-on signals, which indicate power-on state of the first power supplying unit, transmitted from the power supply controlling unit.

Optionally, the controller device may detect power-off state of the at least one of the processor devices by receiving power-off signals, which indicate power-off state of the first power supplying unit, transmitted from the power supply controlling unit.

Optionally, the controller device may transmit data concerning at least one of the processor devices to be activated by the activating signal to the at least one of the processor devices in accordance with the output of the activating signal.

Optionally, the data to be transmitted by the controller device may include identifying information of an observation object to be inspected by the at least one of the processor devices.

Optionally, the data, transmitted to the at least one processor device and received by the at least one processor device, may be associated with identifying data of the at least one of the processor devices and stored in the at least one of the processor devices.

Optionally, the at least one of the processor devices may include a storage area to store information concerning an operation having been performed by using the at least one of the processor devices, the information being stored in association with the identifying information of the observation object. The at least one of the processor devices may transmit the information concerning the operation being associated with the identifying information of the observation object to the controller device in response to the inactivating signal output from the controller device.

According to another aspect of the invention, there is provided a computer usable medium including computer readable instructions for controlling power supply within an endoscope system. The endoscope system has a plurality of processor devices, each of which having a detachably attached endoscope and a controller device, which is communicably connected with the plurality of processor devices. The power supply within the endoscope system is controlled by executing outputting at least one of an activating signal to activate at least one of the processor devices and an inactivating signal to inactivate at least one of the processor devices from the controller device to the at least one of the processor devices, and performing at least one of switching power on to a power supplying unit of the at least one of the processor devices, which supplies the at least one of the processor devices with activating power, according to the activating signal and switching the power off to the first power supplying unit of the at least one of the processor devices according to the inactivating signal.

According to another aspect of the invention, there is provided a processor device with a detachably attached endoscope having a first power supplying unit to supply the processor device with activating power, a power supply controlling unit, which is driven by preparatory power and is capable of at least one of switching on the first power supplying unit according to an activating signal transmitted from an external controller and switching off the first power supplying unit according to an inactivating signal transmitted from the external controller, and a second power supplying unit to supply the preparatory power to the power supply controlling unit.

Optionally, the processor device may further include a storage area to store information concerning an operation having been performed by using the processor device, the information being stored in association with identifying information of an observation object to be inspected by the endoscope. The processor device may transmit the information concerning the operation being associated with the identifying information of the observation object to the external controller in response to the inactivating signal.

According to another aspect of the invention, there is provided controller for an endoscope system having a plurality of endoscope processor units. The controller includes a communication system to communicate with the plurality of endoscope processor units, and a controlling unit, which is capable of outputting at least one of an activating signal to activate at least one of the endoscope processor units and an inactivating signal to inactivate at least one of the endoscope processor units.

Optionally, the controller may be capable of detecting power status of the endoscope processor unit by transmitting detecting signals for detecting power status of the at least one of the endoscope processor units to the at least one of the endoscope processor units, and receiving power status signals, indicating the power status of the at least one of the endoscope processor units, transmitted from the at least one of the endoscope processor units.

Optionally, the controller may detect power-on state of the at least one of the endoscope processor units by receiving power-on signals, which indicate power-on state of the at least one of the endoscope processor units, transmitted from the at least one of the endoscope processor units.

Optionally, the controller may detect power-off state of the at least one of the endoscope processor units by receiving power-off signals, which indicate power-off state of the at least one of the endoscope processor units, transmitted from the at least one of the endoscope processor units.

Optionally, the controller may transmit data concerning the at least one of the endoscope processor units to be activated by the activating signal to the at least one of the endoscope processor units in accordance with the output of the activating signal.

Optionally, the data to be transmitted by the controller may include identifying information of an observation object to be inspected by the at least one of the endoscope processor units.

DETAILED DESCRIPTION OF THE EMBODIMENTS

Figure 1:
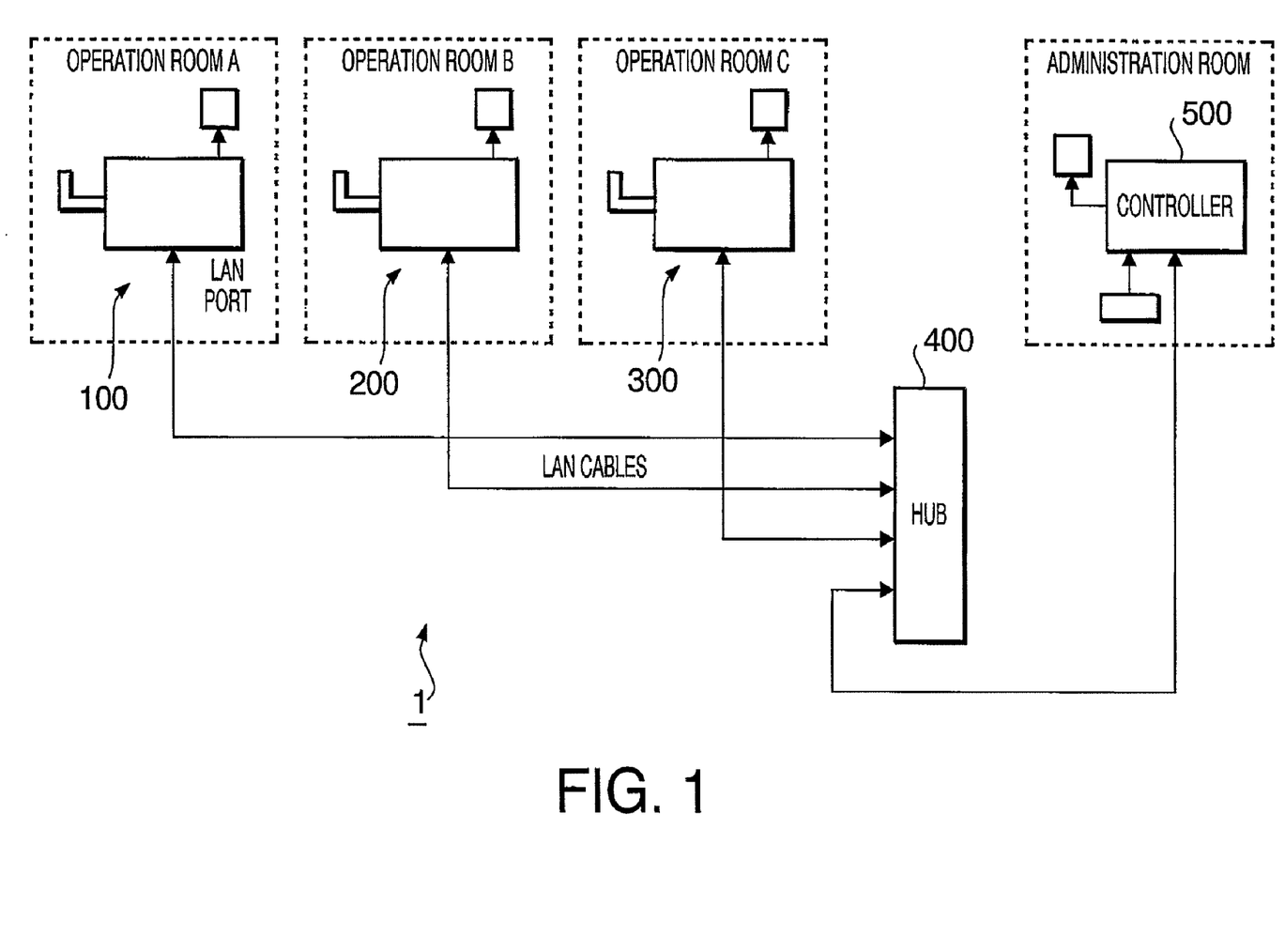
FIG. 1 is a block diagram to illustrate a configuration of an endoscope system according to an embodiment of the present invention.

Hereinafter, referring to the accompanying drawings, an illustrative embodiment of the invention will be described. FIG. 1 is a block diagram to illustrate a configuration of an endoscope system 1 according to an embodiment of the present invention.

The endoscope system includes endoscope unit 100, 200, 300, which are provided in operation rooms A, B, C respectively. A controller 500 of the endoscope system 1 is located in an administration room, which is remote from the operation rooms A, B, C. Each of the endoscope units 100, 200, 300 is connected to a hub 400 through a LAN cable, which is connected to the controller 500. In each of the operation rooms A, B, C, operations with each endoscope unit 100, 200, or 300 are performed. Thus, the endoscope units 100, 200, 300 can communicate with the controller 500 through the LAN cables and the hub 400 in order to exchange various data including image data obtained through the endoscope units 100, 200, 300. Further, the controller 500 in the administration room can control power supply to the endoscope units 100, 200, 300 through the network, which includes the LAN cables and the hub 400.

Figure 2:
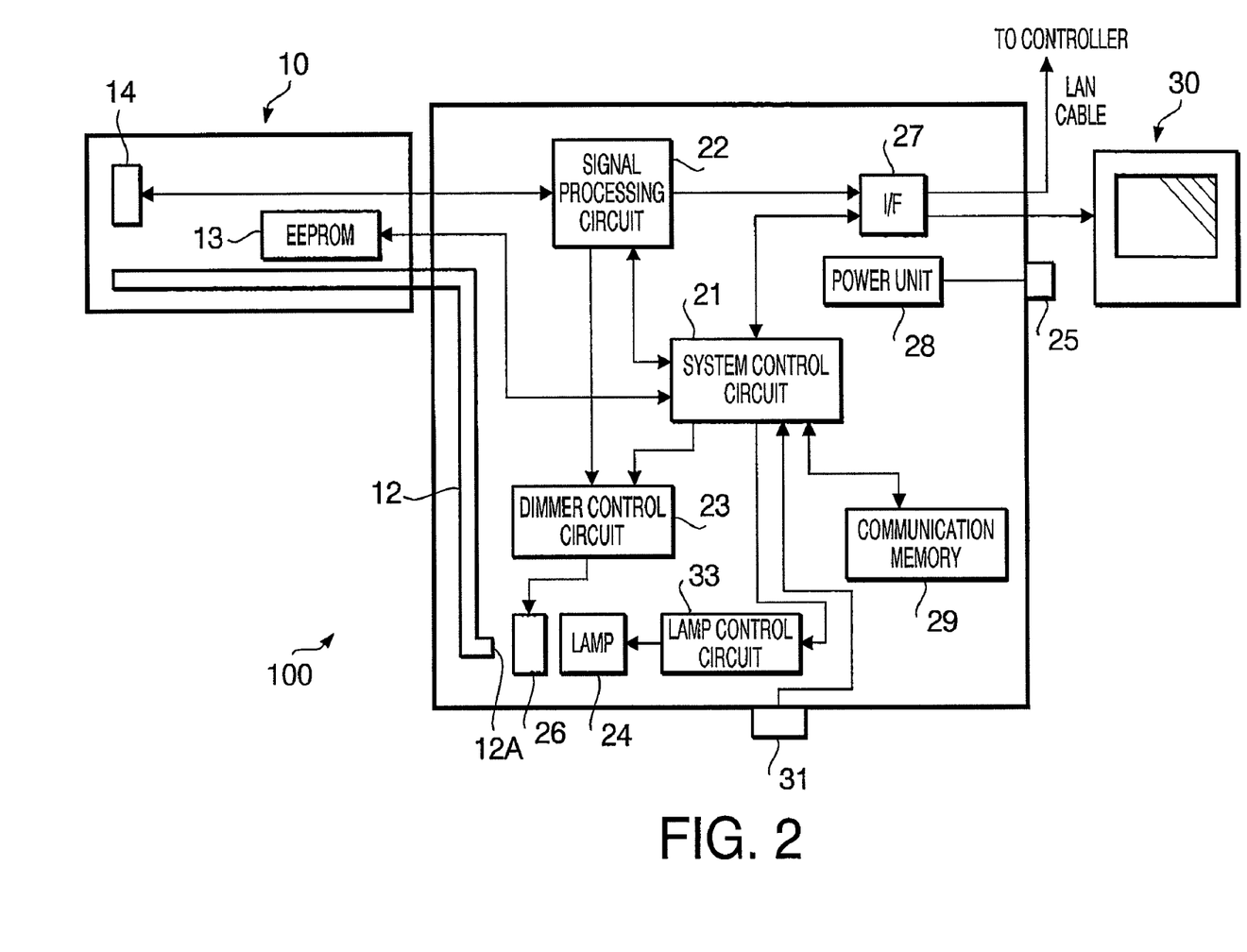
FIG. 2 is a block diagram to illustrate a configuration of an endoscope unit in one of operation rooms according to the embodiment of the present invention.

FIG. 2 is a block diagram to illustrate a configuration of the endoscope unit 100 in the operation room according to the embodiment of the present invention. It is noted that the endoscope units 200, 300 are in the identical configuration to the endoscope unit 100, and description of those will be omitted.

The endoscope unit 100 is provided with a processor 20, which is connected with a monitor 30, and a video scope 10, which is detachably attached to the processor 20. The processor 20 is further connected with a keyboard (not shown), which is operated by an operator in the operation room A. A power unit 28 in the processor 20 distributes power to each circuit in the endoscope unit 100 (200, 300) in accordance with an operation given to a main power switch 25. However, electrical connection between the power unit 28 and each circuit is omitted in FIG. 2.

The processor 20 is provided with a lamp 24, which is supplied with power from a lamp control circuit 33 and lit according to an operation given to a lamp button 31. Light emitted from the lamp 24 is transmitted through a collecting lens (not shown) and enters a light guide 12 from an incidence end 12A. The light guide 12, which is configured with a bundle of optical fibers, transmits the light from the lamp 24 to a distal end portion of the video scope 10, and the transmitted light is emitted through a distributing lens (not shown) to illuminate an observation object.

The emitted light is reflected by the observation object and enters an objective lens (not shown) to reach to a light receiving surface (not shown) of a CCD (charge coupled device) 14. Thus, an image of the observation object is formed on the light receiving surface of the CCD 14, and image signals according to the image are generated. The generated image signals are read from the CCD 14 at a predetermined interval and transmitted to a signal processing circuit 22 of the processor 20. An operation to read the image signals from the CCD 14 is controlled by a CCD driver (not shown), which is provided in the signal processing circuit 22. In the present embodiment, the image signals for one frame are read at an interval of 1/60 second according to a video processing standard (e.g., NTSC.)

The image signals are processed in the signal processing circuit 22 to adjust various settings, such as white balance and gamma correction to generate video signals according to the predetermined video standard. The generated video signals are transmitted to the monitor 30 through an I/F (interface) circuit 27. Thus, the image of the observation object is displayed in the monitor 30. In addition, the signal processing circuit 22 generates brightness signals according to the image signals.

A system control circuit 21, having a CPU (not shown), a ROM (not shown), and a RAM (not shown), controls operations of the endoscope unit 100 (200, 300) and outputs controlling signals to each circuit in the processor 20. Programs for controlling the operations are stored in the ROM. The video scope 10 is provided with an EEPROM 13, which stores data concerning the video scope 10 such as a model number and a serial number of the video scope 10. When the video scope 10 is attached to the processor 20, the data concerning the video scope 10 is transmitted from the EEPROM 13 to the RAM of the system control circuit 21.

A diaphragm 26 is driven by a driving mechanism (not shown) such as a motor to be opened and closed in order to adjust amount of the illumination light emitted from the lamp 24. A dimmer control circuit 23 controls the opening/closing operations of the diaphragm 26 based on brightness data being transmitted from the signal processing circuit 22 so that the image of the observation object displayed in the monitor 30 can be maintained in preferable amount of light.

The system control circuit 21 communicates with the controller 500 in the administration room according to a communication protocol such as TCP/IP through the I/F circuit 27 to exchange data with the controller 500. The exchanged data is stored in a communication memory 29, which is connected with the system control circuit 22.

Figure 3:
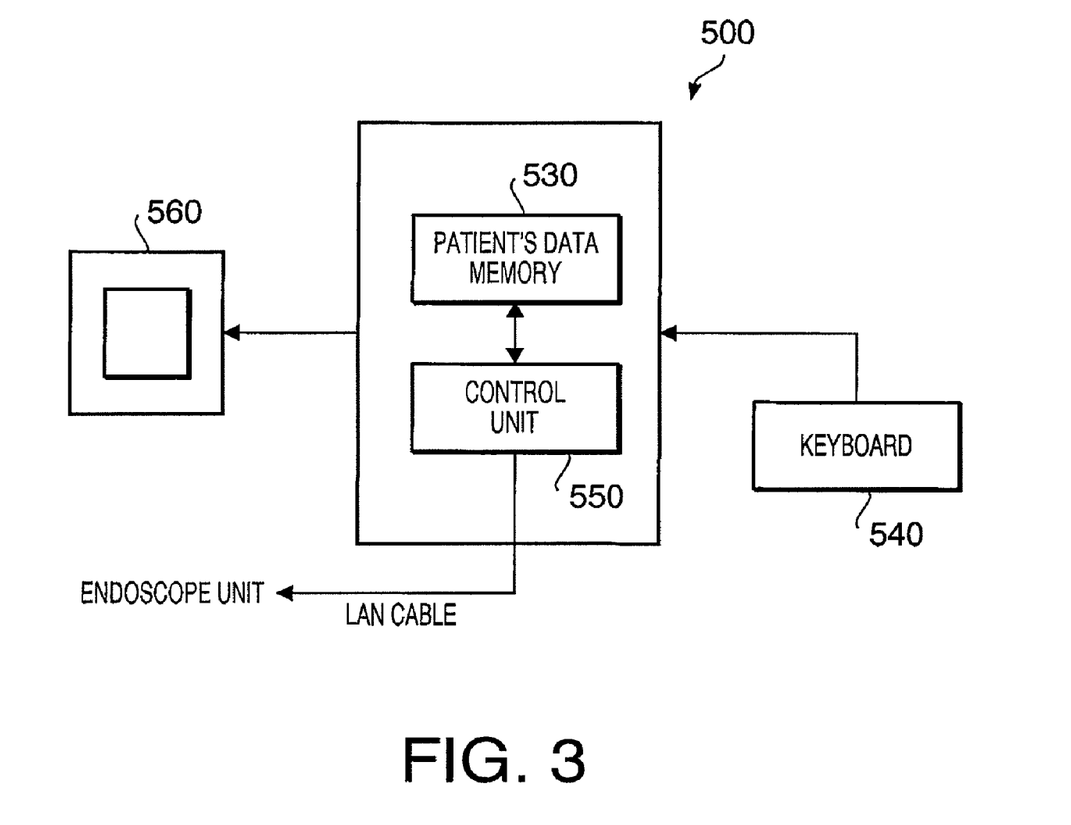
FIG. 3 is a block diagram to illustrate a configuration of a controller of the endoscope system according to the embodiment of the present invention.

FIG. 3 is a block diagram to illustrate a configuration of the controller 500 of the endoscope system according to the embodiment of the present invention. The controller 500 is connected with a keyboard 540 and a monitor 560. The data exchange between the controller 500 and the endoscope units 100, 200, 300 is performed as the operator gives a predetermine input to the controller 500 through the keyboard 540. The controller 500 is provided with a patient's data memory 530, which stores identification data of a patient to be inspected, and a control unit 550, which controls the operations of the controller 500.

Figure 4:
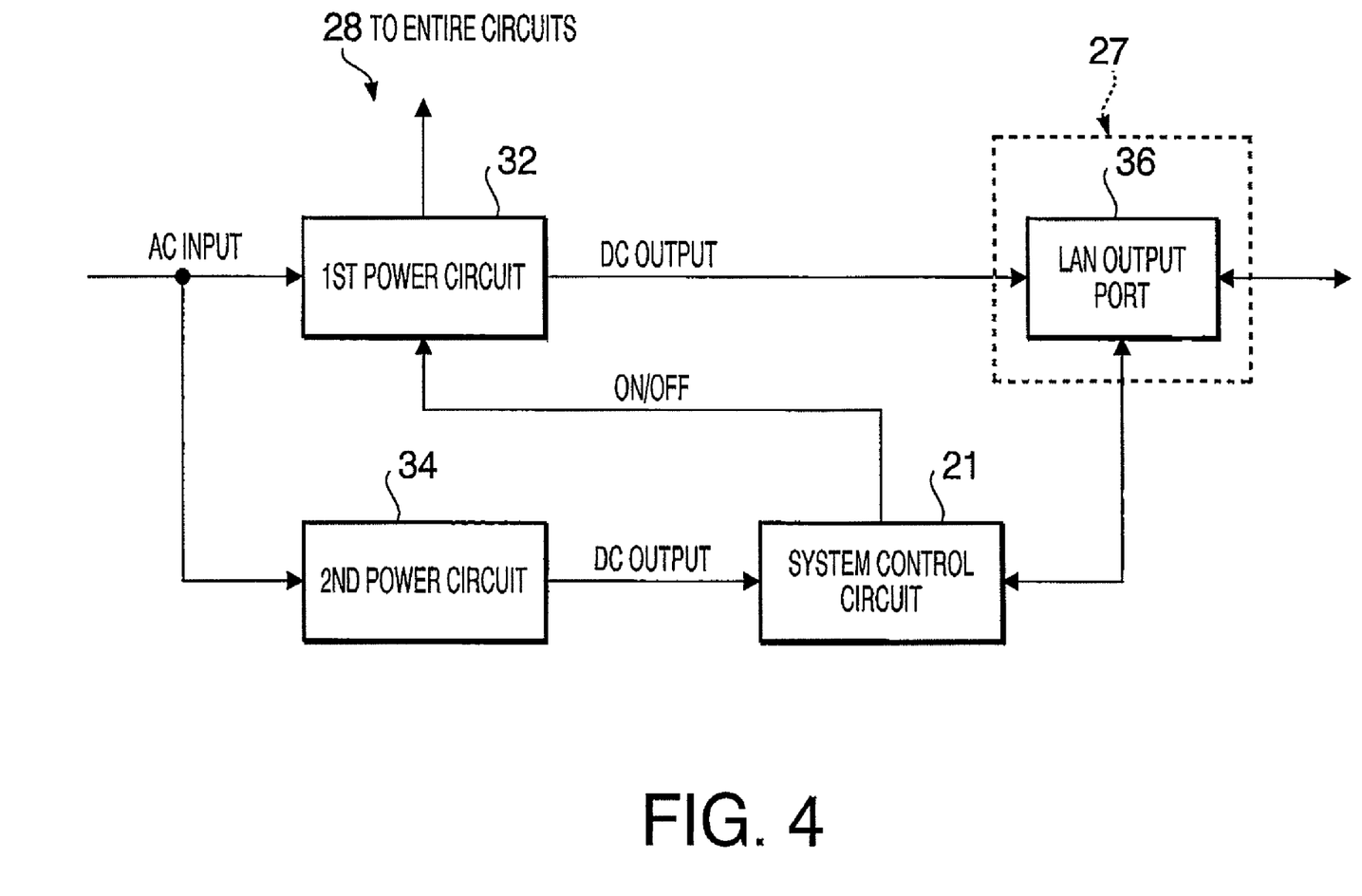
FIG. 4 is a block diagram to illustrate a power unit of the endoscope unit according to the embodiment of the present invention.

FIG. 4 is a block diagram to illustrate the power unit 28 of the endoscope unit 100 according to the embodiment of the present invention. It is noted that the endoscope units 200, 300 are respectively provided with a power unit identical to the power unit 28, therefore, description for the power units of the endoscope units 200, 300 will be omitted.

The power unit 28 includes a first power circuit 32 and a second power circuit 34. Alternating current provided from a commercial power source is inputted to the first power circuit 32 and the second power circuit 34 to be converted into DC current. The DC current converted in the first power circuit 32 is provided to the circuits in the entire processor 20 in order to activate the processor 20. The first power circuit 32 is switched ON/OFF according to the control signals from the system control circuit 21. When the first power circuit is on, the entire processor 20 can be supplied with the power from the first power circuit.

The second power circuit 34, which is provided with power from the commercial power source, constantly supplies power to the system control circuit 21. Further, the second power circuit 34 supplies a LAN output port 36 of the I/F circuit 27 through the system control circuit 21. The second power circuit 34 is provided exclusively to supply power to a circuit which is necessary to activate the endoscope unit 100 (200, 300) for so-called sleep mode setting, therefore, the DC current output from the second power circuit 34 is notably small with respect to the DC current output from the first power circuit 32.

Figure 5:
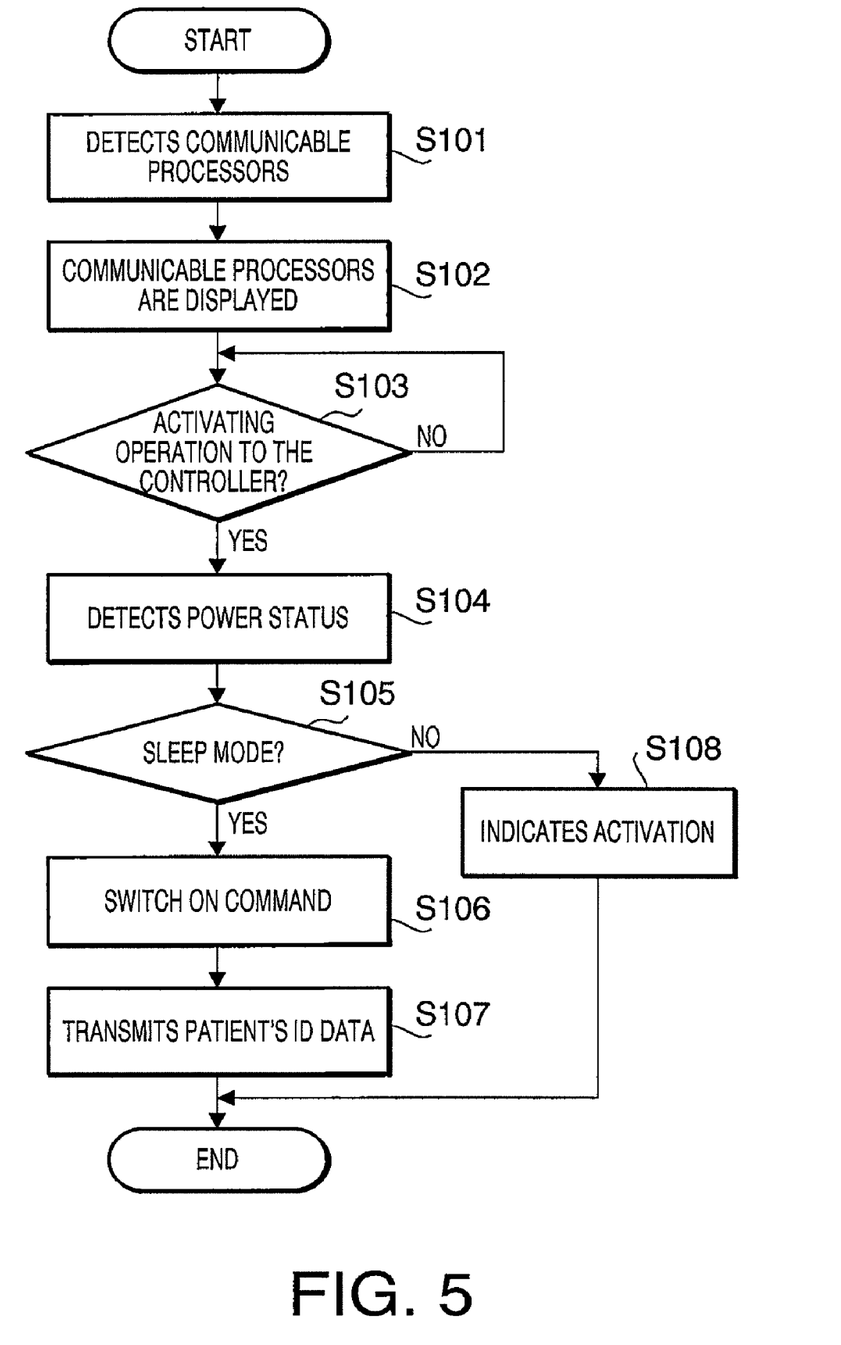
FIG. 5 is a flowchart to illustrate a power-on control process to be executed in the controller of the endoscope system according to the embodiment of the present invention.

FIG. 5 is a flowchart to illustrate a power-on control process to be executed in the controller 500 of the endoscope system 1 according to the embodiment of the present invention. As the process starts, in S101, the controller 500 transmits signals for detecting communicable endoscope units to the processors 20 of the endoscope units 100, 200, 300 in the endoscope system 1. In the present embodiment, each endoscope unit is installed with TCP/IP driver and is assigned an address to identify its location. The addresses of the endoscope units 100, 200, 300 are stored in a storage device (not shown) of the controller 500 so that the controller 500 transmits the detecting signals to the endoscope units 100, 200, 300 based on the addresses.

As one of the endoscope units 100, 200, 300 being connected with the controller 500 through the LAN cable receive the transmitted signals, receipt acknowledgement, i.e., signals indicating the detecting signals is received by the endoscope unit, is transmitted through the LAN output port 36 to the controller 500 on an endoscope unit basis. If any of the endoscope units 100, 200, 300 is not connected and incommunicable with the controller 500, the processor 20 does not receive the detecting signals, and no receipt acknowledgement is transmitted to the controller 500. Thus, the communicable endoscope units among the endoscope units 100, 200, 300 are detected.

In S102, information indicating the detected communicable endoscope units is displayed on the monitor 560.

Next, in S103, the controller 500 judges as to whether an operation to power on (activate) one of the detected communicable endoscope units is given by an operator through the keyboard 540 of the controller 500. In the present embodiment, the endoscope unit 100 is selectively specified by the operator who views the information to indicate the detected communicable endoscope units on the monitor 560. If the operation is not detected (S103: NO), the controller repeats S103. If the operation is detected (S103: YES), in S104, the controller 500 outputs signals to detect power status of the processor 20 of the endoscope unit 100. As the processor 20, receiving the signals output from the controller 500 in S104, returns signals indicating the power status of the processor 20 itself, in S105, the controller 500 judges as to whether the processor 20 is in sleep mode, i.e., the first power circuit 32 is turned off, based on the signals returned from the processor 20.

In S105, if it is judged that the processor 20 is in sleep mode (S105: YES), in S106, command data to switch on the first power circuit 32 of the processor 20 is transmitted to the processor 20 of the endoscope unit 100.

Next, in S107, the controller 500 transmits the identification data of a patient to be inspected by using the endoscope unit 100, stored in the patient's data memory 530, to the endoscope unit 100 in accordance with the command data. The identification data includes, for example, a name and an age of the patient and is stored in the patient's data memory 530 in association with an operation room (i.e., the endoscope unit) to be used for the inspection. Therefore, in S107, the identification data of a patient to be inspected in the operation room A, in which the endoscope unit 100 having the processor 20 is installed, is transmitted from the controller 500 to the endoscope unit 100. The operation room A (i.e., the endoscope unit 100) is determined according to a medical condition, diagnosing results, and operation schedules, for example.

Meanwhile, in S105, if it is judged that the processor 20 is not in sleep mode (S105: NO), in S108, information indicating the processor 20 of the endoscope unit 100 is activated is displayed on the monitor 560, and the controller 500 terminates the process. The above described steps S103 through S108 are performed on the processors 20 of the remaining endoscope units 200, 300 respectively which are detected in S101 and of which power switches are controlled by the controller 500.

Figure 6:
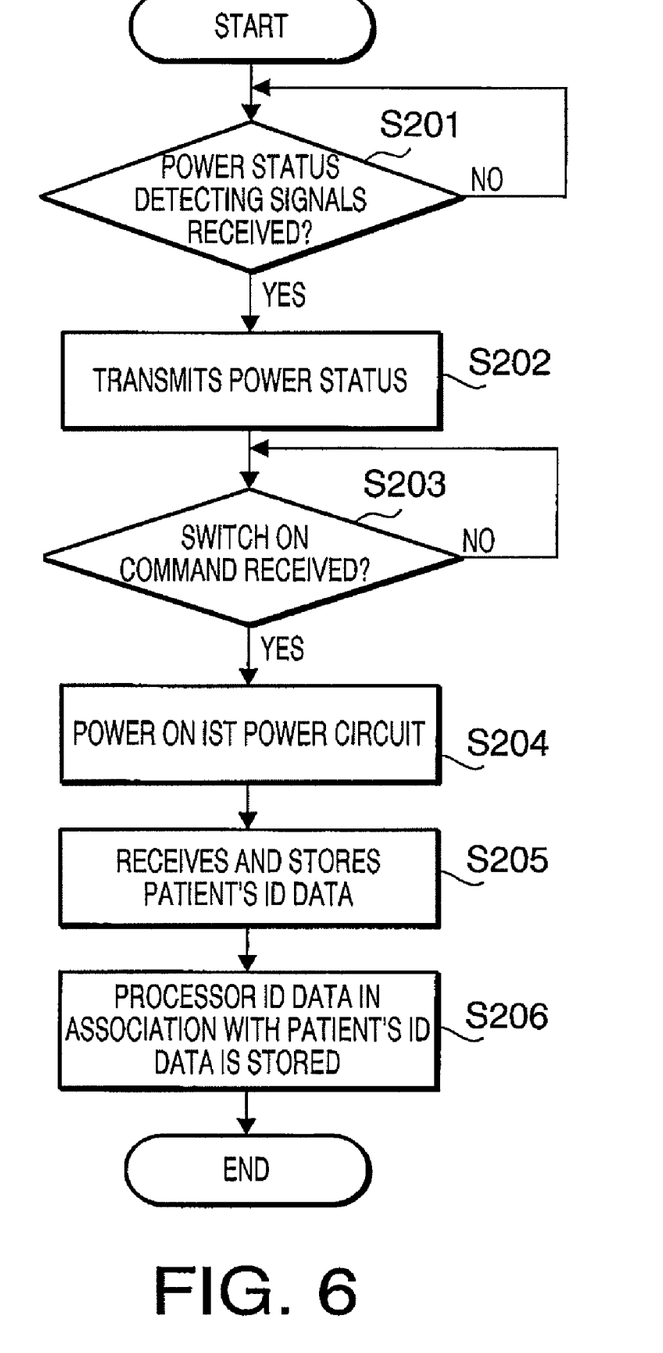
FIG. 6 is a flowchart to illustrate an activation process to be executed by a system control circuit in a processor being activated according to the embodiment of the present invention.

FIG. 6 is a flowchart to illustrate an activation process to be executed by the system control circuit 21 in the processor 20 of the endoscope unit 100 to be activated according to the embodiment of the present invention.

As the activation process starts, in S201, it is judged as to whether the signals, transmitted from the controller 500 in S104 (see FIG. 5), to detect power status of the processors 20 of the endoscope units 100, 200, 300 communicable with the controller 500 are received. If it is judged that the signals are not received (S201: NO), the system control circuit 21 repeats S201. If it is judged that the signals are received (S201: YES), the system control circuit 21 proceeds to S202.

In S202, signals indicating the power status of the processor 20 of the endoscope unit 100, i.e., as to whether the first power circuit 32 is turned off (in sleep mode) or the main power is on, are transmitted to the controller 500 in response to the signals received in S201. Next, in S203, it is judged as to whether the command data to switch on the first power circuit 32 of the processor 20 of the endoscope unit 100, transmitted from the controller 500 in S106, is received. If it is judged that the command data is not received (S203: NO), the system control circuit 21 repeats S203. In S203, if it is judged that the command data is received (S203: YES), the system control circuit 21 proceeds to S204.

In S204, control signals to switch the power to the first power circuit 32 on are output from the system control circuit 21 to the first power circuit 32. Next, in S205, the identification data of the patient to be inspected, transmitted from the controller 500 in S107, is received and stored in a predetermined location of the communication memory 29 of the processor 20 of the endoscope unit 100.

In S206, identification data of the endoscope unit 100 (for example, a model number and a serial number) which has been stored in the ROM (not shown) is read and stored in a predetermined storage area to be associated with the identification data of the patient stored in the communication memory 29. Thereafter, the process is terminated.

Figure 7:
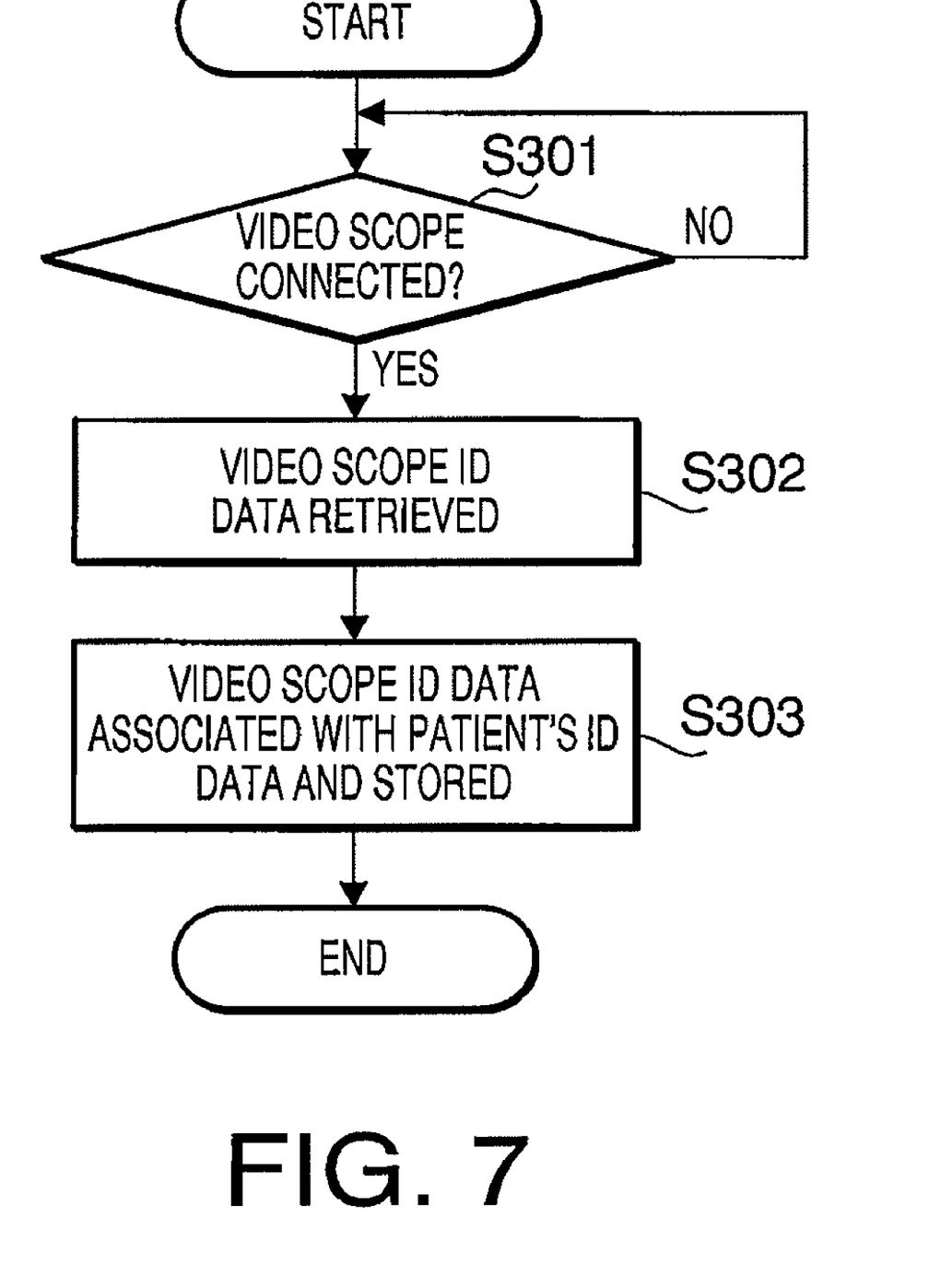
FIG. 7 is a flowchart to illustrate a video scope connection process to be executed by the system control circuit of the processor according to the embodiment of the present invention.

Next, a video scope connection process to be executed by the system control circuit 21 of the endoscope unit 100 (200, 300) will be described. The video scope connection process is executed when the video scope 10 is attached to the processor 20 of the endoscope unit 100. FIG. 7 is a flowchart to illustrate the video scope connection process according to the embodiment of the present invention.

As the process starts, in S301, the system control circuit 21 judges as to whether the video scope 10 is connected to the processor 20 of the endoscope unit 100 based on predetermined signals indicating the connection between the video scope 10 and the processor 20. If it is judged that the video scope 10 is connected (S301: YES), in S302, identification data of the video scope 10, which indicates for example a model number and a serial number of the video scope 10, is retrieved from the EEPROM 13 of the video scope 10 and stored in the RAM of the processor 20. Next, in S303, the identification data of the video scope 10 is associated with the identification data of the patient and stored in a predetermined location of the communication memory 29 of the processor 20. The process terminates thereafter.

Figure 8:
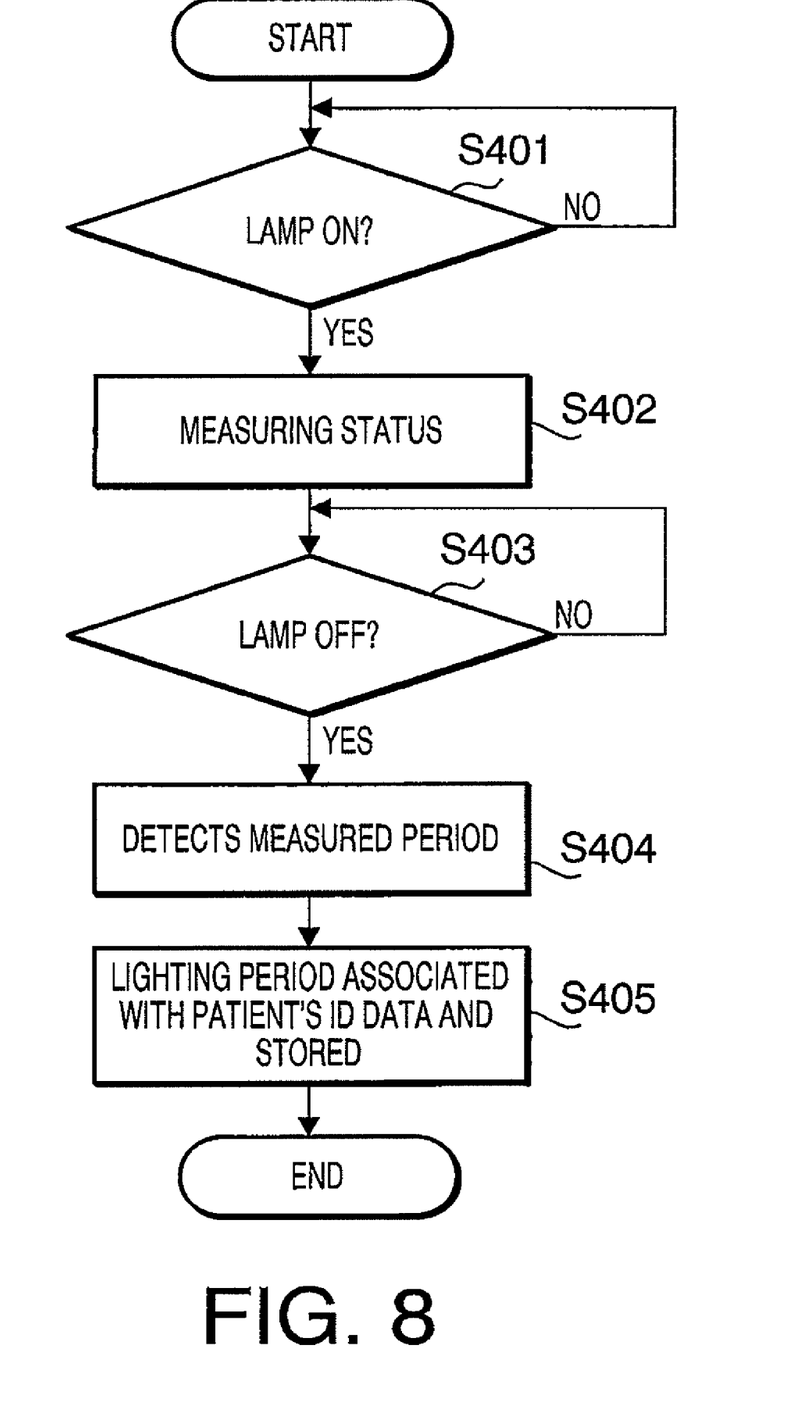
FIG. 8 is a flowchart to illustrate an operation period measuring process to be executed by the system control circuit of the processor according to the embodiment of the present invention.

FIG. 8 is a flowchart to illustrate an operation period measuring process to be executed by the system control circuit 21 of the processor 20 according to the embodiment of the present invention. The operation period measuring process is executed when an operation period, in which the lamp 24 of the endoscope unit 100 (200, 300) is turned on, is measured.

As the process starts, in S401, the system control circuit 21 judges as to whether the lamp button 31 is operated by the operator. As described above, when the lamp button 31 is operated, the lamp 24 is lit to illuminate the observation object. If it is judged that the lamp button 31 is not operated to turn the lamp 24 on (S401: NO), the system control circuit 21 repeats S401. If it is judged that the lamp button 31 is operated (S401: YES), the process proceeds to S402.

In S402, a timer (not shown) provided in the processor 20 of the endoscope unit 100 starts measuring a lighting period of the lamp 24 being lit. In S403, it is judged as to whether the lamp button 31 is operated by the operator to switch off the lamp 24. If it is judged that the lamp button 31 is operated (S403: YES), in S404, the measured period between S402 and S403 is obtained. The process proceeds to S405.

In S405, the measured period is associated with the identification data of the patient and stored in the predetermined location of the communication memory 29. It is noted that generally the lamp 24 is switched on when the endoscope unit 100 (200, 300) including the video scope 10 and the processor 20 is used for an operation and switched off when the operation is terminated. Therefore, the lighting period in which the lamp 24 is on generally corresponds to an operation period using the endoscope unit 100 (200, 300), and the lighting period of the lamp 24 can be considered to be the operation period. Thus, the operation period can be measured in the operation period measuring process as described above.

Figure 9:
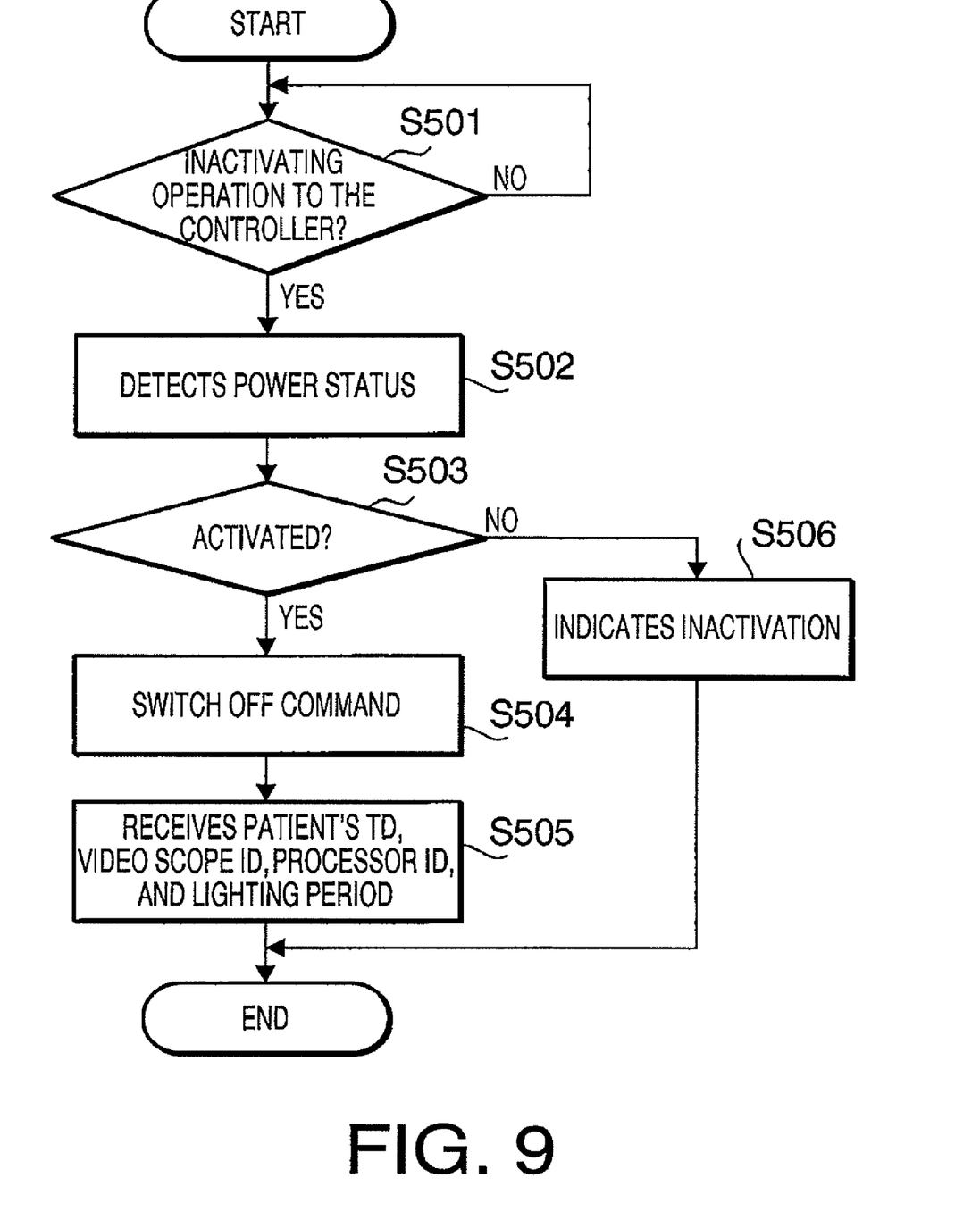
FIG. 9 is a flowchart to illustrate a power-off control process to be executed in the controller of the endoscope system according to the embodiment of the present invention.

FIG. 9 is a flowchart to illustrate a power-off control process to be executed in the controller 500 of the endoscope system 1 according to the embodiment of the present invention. The power-off control process is executed when the processors 20 of the endoscope units 100, 200, 300 communicable with the controller 500 are set to be in the sleep mode. The main power to the endoscope units 100, 200, 300 can be remotely switched off from the administration room through the power-off process of the controller 500 as described below when the operation using the endoscope unit is terminated.

As the process starts, in S501, the controller 500 judges as to whether an operation to switch off (inactivate) the processor 20 of the endoscope unit 100 has been given to the controller 500 by the operator through the keyboard 540. In S502, the controller 500 outputs signals to detect power status of the processor 20. As the processor 20, receiving the signals output from the controller 500 in S502, returns signals indicating the power status of the processor 20 itself, in S503, the controller 500 judges as to whether the first power circuit 32, which can switch on or off the main power to the system control circuit 21, is turned on based on the signals returned from the processor 20.

In S503, if it is judged that the processor 20 is not activated, i.e., in sleep mode (S503: NO), in S506, information indicating the processor 20 of the endoscope unit 100 is inactivated is displayed on the monitor 560, and the controller 500 terminates the process.

In S503, if it is judged that the processor 20 is activated (S503: YES), in S504, command data to switch off the first power circuit 32 of the processor 20 is transmitted to the processor 20.

Next, in S505, the identification data of a patient being inspected by using the endoscope unit 100, the video scope identification data, the processor identification data, and the lighting period, which are associated with the patient's identification data, are stored in the patient's memory 530. The above described steps S501 through 505 are performed on the processors 20 of the remaining endoscope units 200, 300 respectively which are detected in S101 and of which power switches are controlled by the controller 500.

Figure 10:
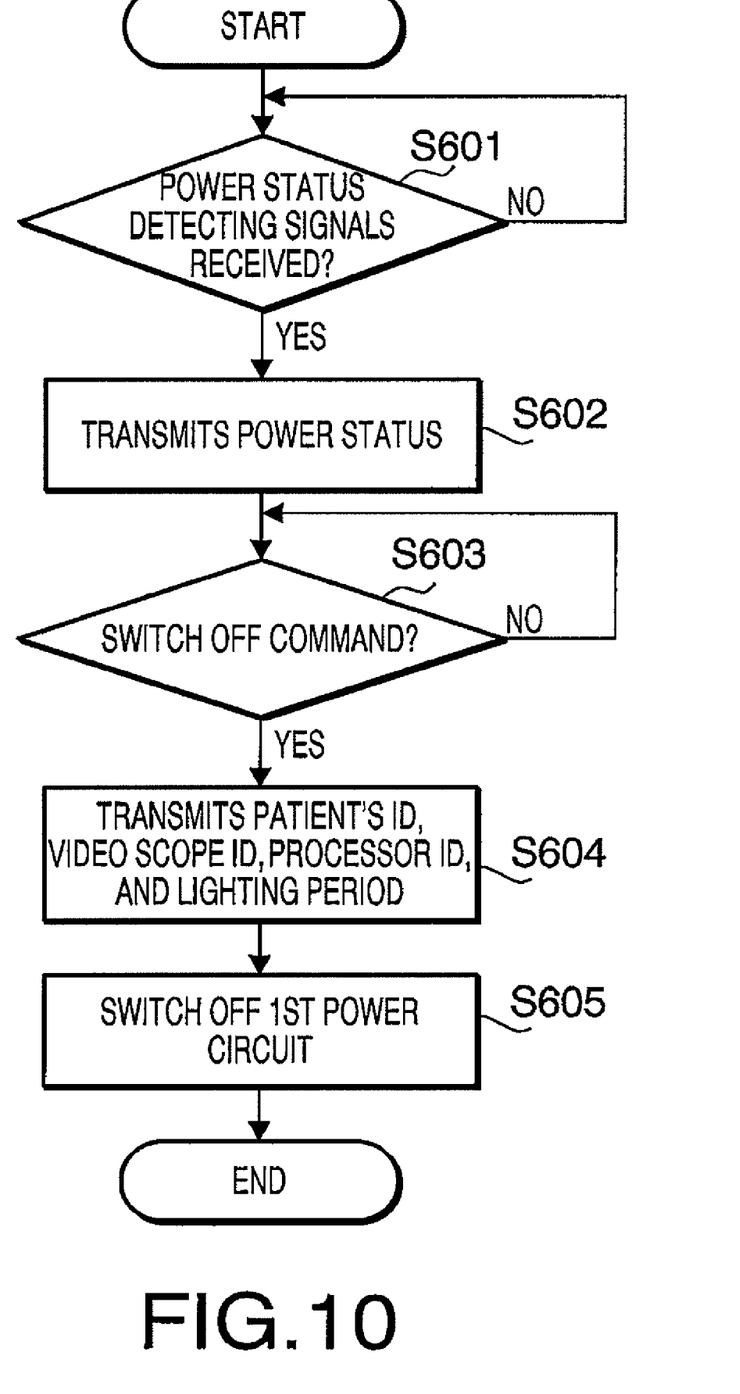
FIG. 10 is a flowchart to be executed by the system control circuit of the processor to be powered off according to the embodiment of the present invention.

FIG. 10 is a flowchart to illustrate a power-off process to be executed, in parallel with the power-off control process, by the system control circuit 21 in the processor 20 of the endoscope unit 100 to be powered off according to the embodiment of the present invention.

As the process starts, in S601, the system control circuit 21 judges as to whether the signals to detect power status of the processor 20, which are transmitted from the controller 500 in S502 (see FIG. 9), are received. If the signals are received (S601: YES), in S602, the system control circuit 21 transmits signals indicating the power status of the processor 20 itself (i.e., either powered on or in sleep mode) to the controller 500. If the signals are not received (S603: NO), the system control circuit 21 repeats S603. Thereafter, in S603, it is judged as to whether the command data to switch off the first power circuit 32 of the processor 20, which is transmitted from the controller 500 in S504, is received.

In S603, if the command data is received (S603: YES), in S604, the system control circuit 21 transmits the patient's identification data along with the associated video scope identification data, the processor identification data, and the lighting period to the controller 500 in response to the command. Consequently, the transmitted identification data is stored in the patient's memory 530 of the controller 500 in S505 (see FIG. 9.)

In S605, the system control circuit 21 outputs controlling signals to switch off the first power circuit 32 according to the command data received in S603.

As described above, the controller 500 is communicably connected to the plurality of endoscope units 100, 200, 300 with the LAN cables while each of the endoscope units 100, 200, 300 is provided with the first power circuit 32 to supply the entire circuits in the processor 20 with the activating and operating power and the second power circuit 34 to supply the system control circuit 21 with the power when the processor 20 is in sleep mode. As the command data to activate the processor 20 from the controller 500 is inputted, the power to the first power circuit 32 is switched on by the system control circuit 21 so that the entire circuits in the processor 21 are supplied with the power. When the command data to inactivate the processor 20 from the controller 500 is received, the power to the first power circuit 32 is switched off by the system control circuit 21 so that the processor 20 is set in sleep mode.

Meanwhile, the identification data of the patient, the processor 20, and the video scope 10 is transmitted to the processor 20 along with the command data to switch on the power of the processor 20. Thus, various data concerning the operation including, for example, a model number and a serial number of the processor 20, a model number and a serial number of the video scope 10 to be connected with the processor 20, and a lighting period for the operation can be stored in association with the patient's identification data. Such data is transmitted to the controller 500 to be administrated when the command data to switch off the processor 20 is transmitted from the controller 500 to the processor 20.

Although an example of carrying out the invention has been described above, the present invention is not limited to the above described embodiment. For example, when the operator gives an operation to the controller 500 to activate the processor 20 of the endoscope unit 100 (200, 300) in the operation room A (B, C), the power switch may be controlled in two phases. That is, it can be configured such that the operator firstly checks the power status of the processor 20 and secondly operates the controller 500 to switch on or off the power of the processor 20. Alternatively, it can be configured such that the operator switches on or off the power of the processor 20 without checking the power status of the processor 20. Further, during the power-off control process, the power status of the processor 20 can be detected by the active/inactive status of the other circuit (e.g., the lamp control circuit 33.) In such configuration, S601 and S602 (FIG. 10) can be omitted.

For another example, the LAN cables in the endoscope system 1 can be replaced with other networking connections, such as wireless communication. Further, the communication protocol is not necessarily TCP/IP, and the processor 20 may be specified by another address specifying method.

Further, transmission of the various identification data of the processor 20, video scope 10, and the lighting period can be omitted so that solely the identification data of the patient is transmitted from the controller 500 to the processor 20 upon activation of the processor 20. The various identification data can be transmitted from the processor 20 to the controller 500 upon inactivation of the processor 20. The various data to be exchanged between the processor 20 and the controller 500 is not limited to the contents as described above.

Furthermore, the second power circuit 34 may be supplied with a power source other than the commercial power source (e.g., a battery.) The power control of the processor 20 may be configured such that solely switching on (or switching off) is controlled by the controller 500.

The present disclosure relates to the subject matter contained in Japanese Patent Application No. P2006-293639, filed on Oct. 30, 2006, which is expressly incorporated herein by reference in its entirety.

What is claimed is:

1. An endoscope system, comprising:
a plurality of processor devices, each having a detachably attached endoscope; and
a controller, which is communicably connected with the plurality of processor devices,
wherein the controller is configured to output at least one of an activating signal to activate at least one of the processor devices and an inactivating signal to inactivate at least one of the processor devices, to the at least one of the processor devices; and wherein each of the plurality of processor devices comprises:
a first power supply that supplies the processor device with activating power;
a power supply controller, which is driven by preparatory power and that switches on the first power supply according to the activating signal and switches off the first power supply according to the inactivating signal, the power supply controller further controlling the endoscope; and
a second power supply that supplies the preparatory power to the power supply controller, the preparatory power being only as much power as necessary to activate the processor device,
wherein the power supply controller does not turn the second power supply on and off,
wherein the first power supply, the second power supply and the power supply controller are integrated into the processor device,
wherein the controller includes an input terminal that receives an operator's power-on input,
upon receiving the operator's power-on input, the controller transmits detecting signals for detecting power status of the first power supply of the at least one of the processor devices to the power supply controller of each of the at least one of the processor devices, and receives power status signals, indicating the power status of the first power supply, transmitted from the power supply controller,
upon receiving a power status signal from one of the plurality of processor devices, the controller determines whether or not the power status signal is a power-off signal, indicating that the first power supply is not currently supplying power to the processor device, and transmits the activation signal to the processor device, upon determining that the power-off signal is received,
wherein after receiving the operator's power-on input, the controller automatically performs the transmission of detecting signals, the reception of the power status signals, and transmission of the activation signal in sequence without the operator's intervention.

2. The endoscope system according to claim 1, wherein the inactivating signal from the controller is output to a selectively specified processor device of the plurality of processor devices.

3. The endoscope system according to claim 1, wherein the controller further detects power-on state of the at least one of the processor devices by receiving power-on signals, which indicate power-on state of the first power supply, transmitted from the power supply controller.

4. The endoscope system according to claim 1, wherein the controller transmits data concerning at least one of the processor devices to be activated by the activating signal to the at least one of the processor devices in accordance with the output of the activating signal.

5. The endoscope system according to claim 4, wherein the data to be transmitted by the controller includes identifying information of an observation object to be inspected by the at least one of the processor devices.

6. The endoscope system according to claim 5, wherein the data, transmitted to the at least one of the processor devices and received by the at least one of the processor devices, is associated with identifying data of the at least one of the processor devices and stored in the at least one of the processor devices.

7. The endoscope system according to claim 6, wherein the at least one of the processor devices includes a storage that stores information concerning an operation having been performed by using the at least one of the processor devices, the information being stored in association with the identifying information of the observation object, and
wherein the at least one of the processor devices transmits the information concerning the operation being associated with the identifying information of the observation object to the controller in response to the inactivating signal output from the controller.

8. A processor device with a detachably attached endoscope, comprising:
a first power supply that supplies the processor device with activating power;
a power supply controller, which is driven by preparatory power and that switches on the first power supply according to an activating signal transmitted from an external controller and switches off the first power supply according to an inactivating signal transmitted from the external controller, the power supply controller further controlling the endoscope; and
a second power supply that supplies the preparatory power to the power supply controller, the preparatory power being only as much power as necessary to activate the processor device,
wherein the power supply controller does not turn the second power supply on and off,
wherein the first power supply, the second power supply and the power supply controller are integrated into the processor device,
wherein the power supply controller receives a detecting signal for detecting power status of the first power supply from the external controller, and transmits a power-off signal to the external controller in response to the detecting signal, when the first power supply is not currently supplying power,
wherein the power supply controller switches on the first power supply unit, when the activating signal is received following the detecting signal.

9. The processor device according to claim 8, further comprising:
a storage that stores information concerning an operation having been performed by using the processor device, the information being stored in association with identifying information of an observation object to be inspected by the endoscope,
wherein the processor device transmits the information concerning the operation being associated with the identifying information of the observation object to the external controller in response to the inactivating signal.

10. The processor device according to claim 8, wherein upon receiving the detecting signal from the external controller, the power supply controller transmits a power-on signal, indicating a power-on state of the first power supply, to the external controller in response to the detecting signal, when the first power supply is currently supplying power,
wherein the power supply controller switches off the first power supply unit, when an inactivating signal is received following the detecting signal.

* * * * *